United States Patent
Hayakawa et al.

(10) Patent No.: US 12,145,829 B2
(45) Date of Patent: Nov. 19, 2024

(54) ASEPTIC FILLING METHOD AND ASEPTIC FILLING MACHINE

(71) Applicant: Dai Nippon Printing Co., Ltd., Tokyo (JP)

(72) Inventors: Atsushi Hayakawa, Tokyo (JP); Yoshinori Satou, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 255 days.

(21) Appl. No.: 17/754,808

(22) PCT Filed: Nov. 10, 2020

(86) PCT No.: PCT/JP2020/041915
§ 371 (c)(1),
(2) Date: Apr. 13, 2022

(87) PCT Pub. No.: WO2021/100557
PCT Pub. Date: May 27, 2021

(65) Prior Publication Data
US 2023/0211995 A1    Jul. 6, 2023

(30) Foreign Application Priority Data

Nov. 21, 2019  (JP) ................... 2019-210610

(51) Int. Cl.
*B67C 3/22*    (2006.01)
*B29C 49/42*   (2006.01)
(Continued)

(52) U.S. Cl.
CPC ...... *B67C 7/0073* (2013.01); *B29C 49/42808* (2022.05); *B29C 49/42822* (2022.05);
(Continued)

(58) Field of Classification Search
CPC ..... B67C 3/007; B67C 3/2642; B67C 7/0073; B67C 2003/227; B67C 2003/228;
(Continued)

(56) References Cited

U.S. PATENT DOCUMENTS

2011/0094616 A1    4/2011   Hayakawa et al.
2014/0144105 A1*   5/2014   Hayakawa et al. ... B67C 7/0073
                                                         53/559
(Continued)

FOREIGN PATENT DOCUMENTS

CN    106239877 A    12/2016
CN    208307415 U     1/2019
(Continued)

OTHER PUBLICATIONS

Japanese Office Action (with English translation) dated Nov. 14, 2023 (Application No. 2021-179035).
(Continued)

*Primary Examiner* — Stephen F. Gerrity
(74) *Attorney, Agent, or Firm* — BURR PATENT LAW, PLLC

(57) ABSTRACT

A preform is heated, the heated preform is sealed in a sealing apparatus including a neck portion mold, a trunk portion mold and a bottom portion mold at a predetermined temperature range, and the heated preform sealed in the molds is blow-molded into a bottle. Any molded bottle is removed if the mold surface temperature of the neck portion mold, the trunk portion mold and the bottom portion mold are outside of the predetermined temperature range. A sterilizer is blasted to any molded bottle not removed when the mold surface temperature of all of the molds is in the predetermined temperature range.

13 Claims, 6 Drawing Sheets

(51) Int. Cl.
*B29C 49/48* (2006.01)
*B29C 49/78* (2006.01)
*B67C 3/26* (2006.01)
*B67C 7/00* (2006.01)
*B29L 31/00* (2006.01)

(52) U.S. Cl.
CPC ........ *B29C 49/4823* (2013.01); *B29C 49/786* (2013.01); *B67C 3/2642* (2013.01); *B29C 2049/4825* (2013.01); *B29C 2049/78645* (2022.05); *B29L 2031/7158* (2013.01); *B67C 2003/227* (2013.01); *B67C 2003/228* (2013.01); *B67C 2007/006* (2013.01); *B67C 2007/0066* (2013.01)

(58) Field of Classification Search
CPC ...... B67C 2007/006; B67C 2007/0066; B65B 55/10; B29C 49/4238; B29C 49/42802; B29C 49/42808; B29C 49/4281; B29C 49/42822; B29C 2049/4889; B29C 2049/7864; B29C 2049/78645; B29C 2049/78675
USPC .................. 53/426, 453, 52, 53, 559, 561
See application file for complete search history.

(56) References Cited

U.S. PATENT DOCUMENTS

| | | | | |
|---|---|---|---|---|
| 2014/0264990 | A1* | 9/2014 | Hollriegl et al. ..... | B29C 49/786 425/143 |
| 2014/0311095 | A1* | 10/2014 | Hayakawa et al. ... | B67C 7/0073 53/167 |
| 2016/0046062 | A1 | 2/2016 | Suga et al. | |
| 2016/0375160 | A1* | 12/2016 | Hayakawa ............ | B67C 7/0073 422/29 |
| 2018/0186057 | A1* | 7/2018 | Hayakawa .............. | B29C 49/46 |
| 2019/0256336 | A1 | 8/2019 | Takaku et al. | |
| 2021/0107780 | A1 | 4/2021 | Hayakawa et al. | |

FOREIGN PATENT DOCUMENTS

| | | | | |
|---|---|---|---|---|
| JP | S57-012618 | A | | 1/1982 |
| JP | H09174673 | A * | 7/1997 | ............ B29C 49/78 |
| JP | H09-295317 | A | | 11/1997 |
| JP | 2000-127234 | A | | 5/2000 |
| JP | 2000190382 | A * | 7/2000 | |
| JP | 2005-169885 | A | | 6/2005 |
| JP | 2006-095906 | A | | 4/2006 |
| JP | 2006-111295 | A | | 4/2006 |
| JP | 2009-280222 | A | | 12/2009 |
| JP | 2010-155631 | A | | 7/2010 |
| JP | 2012-206261 | A | | 10/2012 |
| JP | 2014-208434 | A | | 11/2014 |
| JP | 2017124571 | A * | 7/2017 | |
| JP | 2018-177263 | A | | 11/2018 |
| KR | 10-2015-0005039 | A | | 1/2015 |

OTHER PUBLICATIONS

Japanese Office Action (with English translation) dated Nov. 14, 2023 (Application No. 2022-195365).
International Search Report and Written Opinion (Application No. PCT/JP2020/041915) dated Jan. 12, 2021 (with English translation).
Japanese Office Action (Application No. 2022-195368) dated Aug. 8, 2023 (with English translation) (14 pages).
Japanese Office Action (Application No. 2022-195365) dated Aug. 8, 2023 (with English translation) (12 pages).
Japanese Office Action (Application No. 2021-179035) dated Aug. 8, 2023 (with English translation) (16 pages).
Japanese Office Action (Application No. 2022-195367) dated Aug. 8, 2023 (with English translation) (16 pages).
Japanese Office Action (Application No. 2022-195366) dated Aug. 8, 2023 (with English translation) (16 pages).

* cited by examiner

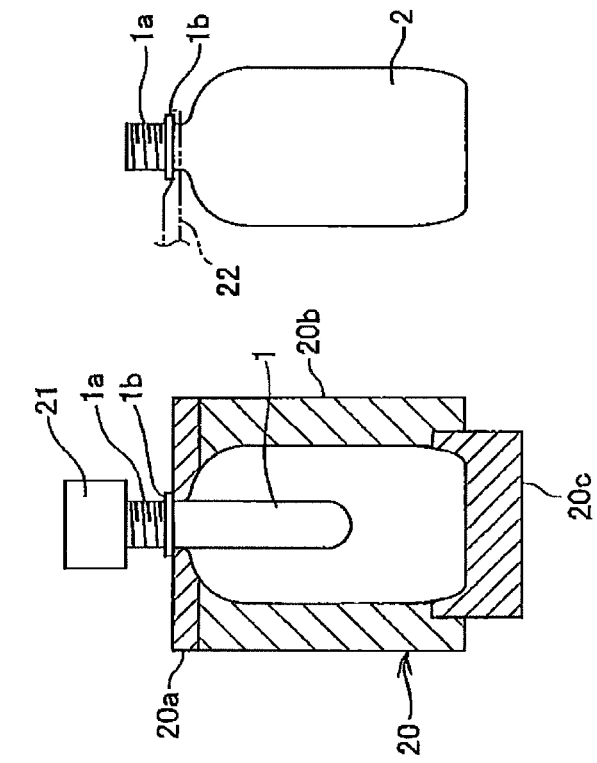
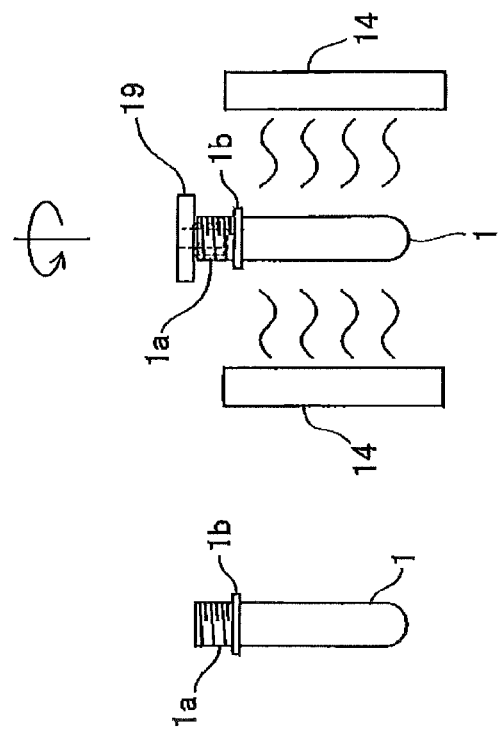

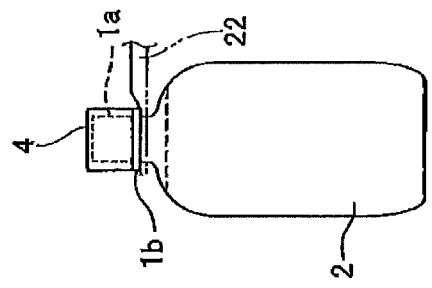
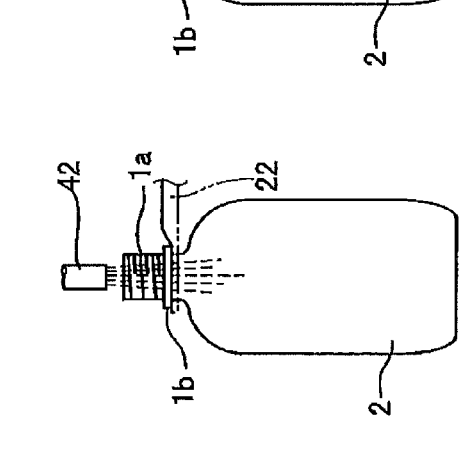
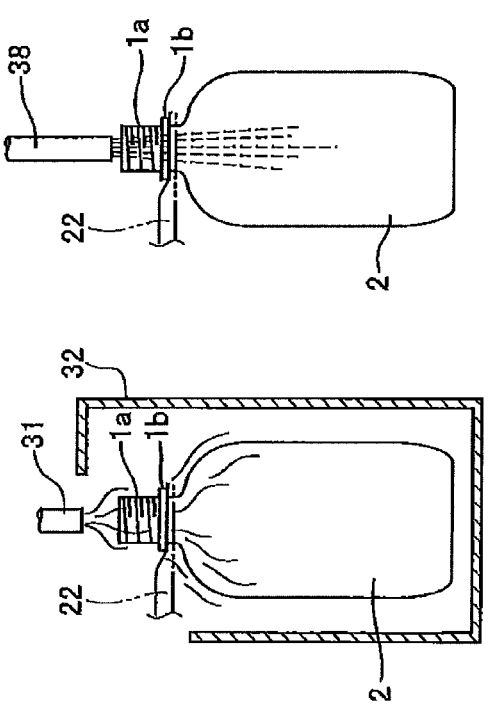
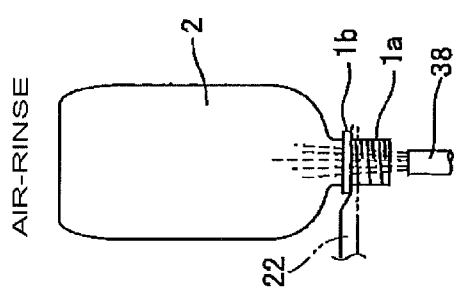
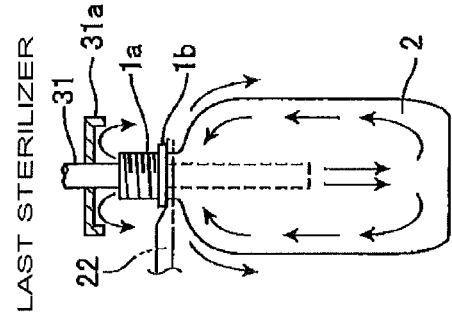

ASEPTIC FILLING METHOD AND ASEPTIC FILLING MACHINE

TECHNICAL FIELD

The present invention relates to an aseptic filling method and an aseptic filling machine that involve molding a preform into a bottle while monitoring the temperature of a mold, sterilizing the molded bottle with a sterilizer, filling the sterilized bottle with a sterilized content, and sealing the bottle filled with the content with a sterilized lid member.

BACKGROUND ART

There is a known aseptic filling machine that includes a molding portion that blow-molds a preform into a bottle, a sterilizing portion that sterilizes the bottle molded in the molding portion with a sterilizer, an air-rinsing portion that air-rinses the bottle sterilized in the sterilizing portion, and a filling portion that fills the bottle air-rinsed in the air-rinsing portion with a content and seals the bottle, the portions being connected to each other, a transfer device being provided for continuously transferring the bottle from the molding portion to the filling portion via the sterilizing portion and the air-rinsing portion, and the part from the molding portion to the filling portion being covered with a chamber. With this aseptic filling machine, the heat applied to the bottle in the molding phase can be used to increase the sterilization effect of a mist of hydrogen peroxide, which is used as the sterilizer (see Patent Literature 1).

There is another known aseptic filling machine that inspects the temperature of bottles molded from preforms, conveys only the bottles the surface temperature of which is confirmed to be equal to or higher than a certain temperature to a sterilizing portion and removes any bottle the surface temperature of which is lower than the certain temperature (see Patent Literature 2).

CITATION LIST

Patent Literature

Patent Literature 1: Japanese Patent Laid-Open No. 2006-111295
Patent Literature 2: Japanese Patent Laid-Open No. 2010-155631

SUMMARY OF INVENTION

Technical Problem

With conventional aseptic filling machines, molding of bottles, sterilization of the bottles, and filling the bottles with a drink can be continuously performed. However, all the molded bottles are fed to the sterilization step and the filling step, and therefore, there is a risk that a faulty bottle may be filled with a drink and shipped. For example, if a bottle insufficiently heated is fed to the sterilization step, there is a risk that the sterilization may be inadequate, and that such a bottle may be filled with a drink and shipped.

In view of this, in Patent Literature 2, the surface temperature of the molded bottles is measured, and only the bottles the surface temperature of which is equal to or higher than a certain temperature are conveyed to the sterilizing portion. However, the filling rate of aseptic filling machines, which was 600 bottles/minute in the past, is now 1000 bottles/minute or higher. Although the surface temperature of the bottles can be measured without problems at the rate of 600 bottles/minute or so, the accuracy of the measurement of the surface temperature of the bottles is insufficient at the rate of 1000 bottles/minute or higher. The surface temperature of the bottle is measured at the neck portion, the trunk portion and the bottom portion of the bottle. In particular, the neck portion is threaded and thus has surface irregularities, which cause irregular reflection of the infrared radiation emitted from the measured part, and therefore, the temperature cannot be accurately measured when the filling rate is high.

Therefore, there is a demand for an aseptic filling machine that keeps the surface temperature of molded bottles equal to or higher than a certain temperature and adequately sterilizes the bottles with a sterilizer even when the filling rate is high.

An object of the present invention is to provide an aseptic filling method and an aseptic filling machine that can solve the problems described above.

Solution to Problem

To solve the problems described above, the present invention is configured as follows.

An aseptic filling method according to the present invention is an aseptic filling method, wherein when a preform is heated, the heated preform is sealed in a neck portion mold, a trunk portion mold and a bottom portion mold at a temperature in a predetermined temperature range, and the preform sealed in the molds is blow-molded into a bottle, any bottle is removed which has been molded in the neck portion mold, the trunk portion mold and the bottom portion mold the temperature of any of which is outside the predetermined temperature range, a sterilizer is brought into contact with any bottle that has not been removed to sterilize a surface of the bottle, the sterilized bottle is filled with a sterilized content, and the bottle filled with the content is sealed with a sterilized lid member.

Further, in the aseptic filling method according to the present invention, preferably, the temperature of the neck portion mold, the trunk portion mold and the bottom portion mold in the predetermined temperature range is a surface temperature of the molds, the surface temperature of the molds is measured with a sensor, and an angle formed by a straight line extending from a tip end of the sensor and a normal to a measured surface of the molds is equal to or less than 60 degrees.

Further, in the aseptic filling method according to the present invention, preferably, the surface temperature of the molds is a temperature of the molds opened immediately after the preform is blow-molded into the bottle.

Further, in the aseptic filling method according to the present invention, preferably, the temperature of the neck portion mold, the trunk portion mold and the bottom portion mold in the predetermined temperature range is a temperature of a mold temperature adjusting medium circulated through the molds.

Further, in the aseptic filling method according to the present invention, preferably, the sterilizer is a gas or mist of a sterilizer or a mixture thereof.

An aseptic filling machine according to the present invention is an aseptic filling machine, including: a heating apparatus that heats a preform; a neck portion mold, a trunk portion mold and a bottom portion mold in which the heated preform is sealed in order to blow-mold the preform into a bottle; a mold temperature adjusting apparatus that adjusts a temperature of the neck portion mold, the trunk portion mold and the bottom portion mold to fall within a predetermined temperature range; a blow-molding apparatus that blow-molds the preform sealed in the molds into the bottle; a bottle removing apparatus that removes any bottle that has been molded in the neck portion mold, the trunk portion mold and the bottom portion mold the temperature of any of which is outside the predetermined temperature range; a bottle sterilizing apparatus that sterilizes any bottle that has not been removed by blasting a sterilizer to the bottle; a filling apparatus that fills the sterilized bottle with a sterilized content; a sealing apparatus that seals the bottle filled with the content with a sterilized lid member; and a conveying apparatus that conveys the preform or the bottle from the heating apparatus to the sealing apparatus.

Further, in the aseptic filling machine according to the present invention, preferably, the mold temperature adjusting apparatus includes a mold surface temperature measuring apparatus that measures a surface temperature of the neck portion mold, the trunk portion mold and the bottom portion mold, the mold surface temperature measuring apparatus comprises a sensor that measures the surface temperature of the molds, and an angle formed by a straight line extending from a tip end of the sensor and a normal to a measured surface of the molds is equal to or less than 60 degrees.

Further, in the aseptic filling machine according to the present invention, preferably, the mold surface temperature measuring apparatus measures a surface temperature of an inner surface of the neck portion mold, the trunk portion mold and the bottom portion mold opened immediately after the preform is blow-molded into the bottle.

Further, in the aseptic filling machine according to the present invention, preferably, the mold temperature adjusting apparatus includes a circulating apparatus that circulates a mold temperature adjusting medium through the neck portion mold, the trunk portion mold and the bottom portion mold, and a mold temperature adjusting medium temperature measuring apparatus that measures a temperature of the mold temperature adjusting medium for all of the molds when the mold temperature adjusting medium flows into and flows out of each of the neck portion mold, the trunk portion mold and the bottom portion mold.

Further, in the aseptic filling machine according to the present invention, preferably, the mold temperature adjusting apparatus stops circulating the mold temperature adjusting medium through the molds when the temperature of the mold temperature adjusting medium flowing into and flowing out of the molds is outside the predetermined temperature range.

Advantageous Effects of Invention

The bottle sterilization effect is improved by bringing the inner and outer surfaces of a bottle produced by blow-molding a heated preform into contact with a sterilizer while the heat applied to the preform remains in the bottle. In order that adequate heat remains in the molded bottle, the temperature of the mold unit used for blow-molding the heated preform needs to fall within a predetermined temperature range. The preform is sealed in a mold unit formed by three molds corresponding to a neck portion, a trunk portion and a bottom portion of the bottle to be blow-molded, an extension rod is inserted into the preform, and high-pressure air is blasted to the preform to blow-mold the preform into the bottle. The surface of the bottle blow-molded is shaped to conform to the shape of the neck portion mold, the trunk portion mold and the bottom portion mold, and the surface of the molds is in contact with the outer surface of the bottle immediately after the molding. Therefore, the surface temperature of the neck portion, the trunk portion and the bottom portion of the bottle with which the sterilizer comes into contact is determined by the temperature of the molds.

The present application provides an aseptic filling method and an aseptic filling machine that can improve the sterilization effect of the sterilizer by controlling the surface temperature of the molds to fall within a predetermined temperature range so that the heat applied to the preform remains in the blow-molded bottle. Further, according to the invention of the present application, since the sterilization effect is improved, the amount of the sterilizer coming into contact with the bottle can be reduced. Further, since the amount of the sterilizer is reduced, the amount of the sterilizer remaining in the bottle can be reduced.

BRIEF DESCRIPTION OF DRAWINGS

FIGS. 2(A)-2(D) show steps performed by a heating apparatus and a blow-molding apparatus of the aseptic filling machine according to the embodiment of the present invention, FIG. 2(A) showing a preform supplying step, FIG. 2(B) showing a preform heating step, FIG. 2(C) showing a blow-molding step, and FIG. 2(D) showing a bottle removal step.

FIGS. 3(E-1), 3(E-2), 3(F-1), 3(F-2), 3(G) and 3(H) show steps performed by a bottle sterilizing apparatus and a filling apparatus of the aseptic filling machine according to the embodiment of the present invention, FIG. 3(E-1) showing a sterilizer blasting step performed with a bottle being shielded with a tunnel, FIG. 3(E-2) showing a sterilizer blasting step performed by inserting a sterilizer blasting nozzle into the bottle, FIG. 3(F-1) showing an air-rinsing step with the bottle in an upright position, FIG. 3(F-2) showing an air-rinsing step with the bottle in an inverted position, FIG. 3(G) showing a filling step, and FIG. 3(H) showing a sealing step.

DESCRIPTION OF EMBODIMENTS

In the following, an embodiment of the present invention will be described with reference to the drawings.

Figure 1:
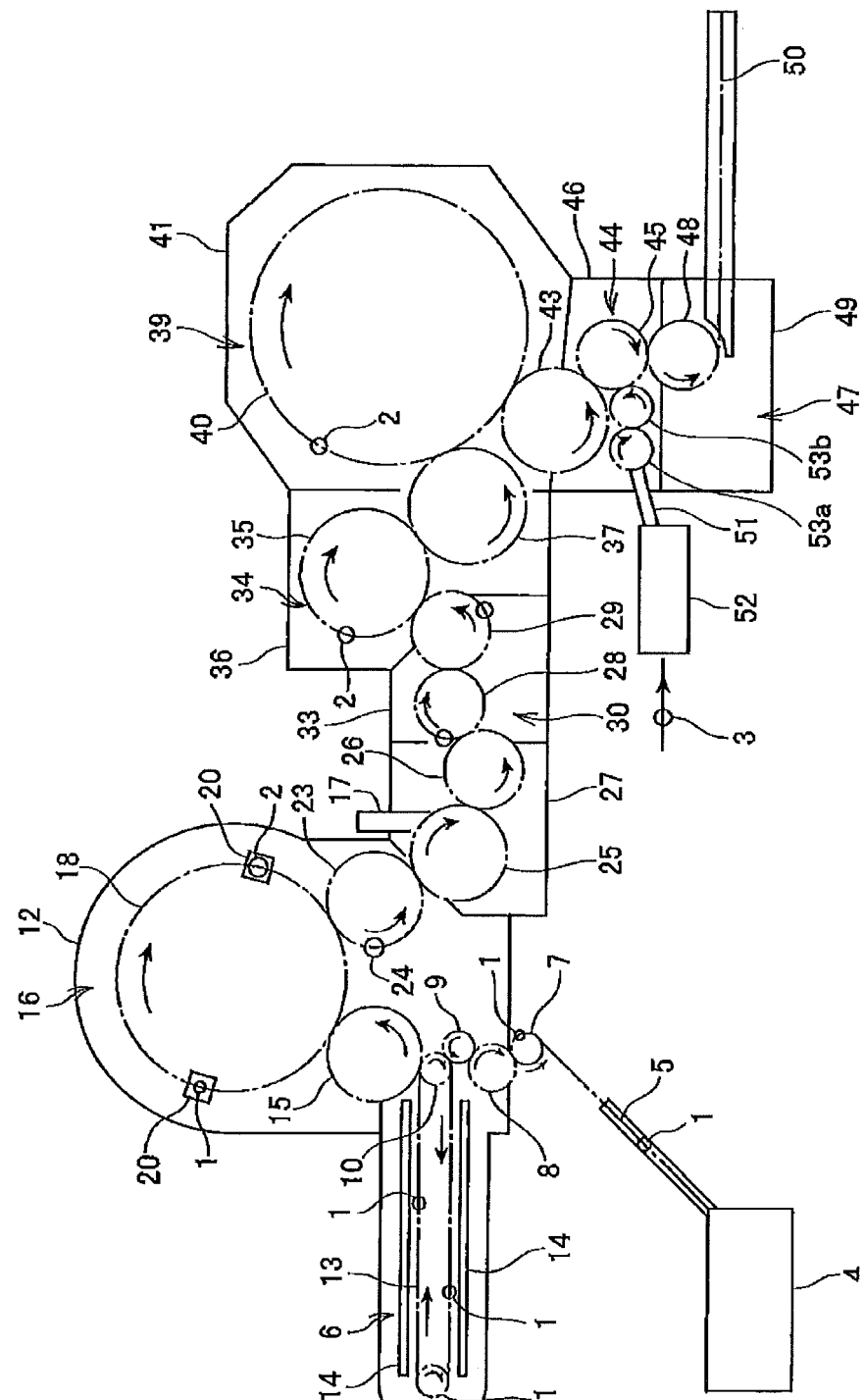
FIG. 1 is a plan view schematically showing an aseptic filling machine according to an embodiment of the present invention.

FIG. 1 shows an aseptic filling machine according to the present invention. With reference to FIG. 1, an aseptic filling machine will be summarized which includes a heating apparatus that heats a preform supplied, a blow-molding apparatus that blow-molds the preform into a bottle, a bottle removing apparatus that removes any bottle blow-molded with a mold for a neck portion, a mold for a trunk portion and a mold for a bottom portion the temperature of any of which is outside a predetermined temperature range, a bottle sterilizing apparatus that sterilizes the bottle, a filling apparatus that fills the bottle with a content, and a sealing apparatus that seals the bottle filled with the content. Details of steps performed by each apparatus will be then described with reference to FIG. 2, FIG. 3, and FIG. 4. According to this embodiment, when a preform is heated and blow-molded into a bottle, the applied heat can be properly retained in the bottle and causes no deformation of the blow-molded bottle.

Summary of Embodiment

As shown in FIG. 1, the aseptic filling machine according to this embodiment includes a preform supplying apparatus 4 that supplies a preform 1, a heating apparatus 6 that heats the preform 1 to a temperature for molding the preform 1 into a bottle 2, a blow-molding apparatus 16 that molds the heated preform 1 into the bottle 2, a bottle inspecting apparatus 24 that inspects the appearance of the blow-molded bottle 2, a bottle removing apparatus 17 that removes any bottle 2 that has been blow-molded in a mold unit 20 included in the blow-molding apparatus 16 that is at a temperature outside a predetermined temperature range, a bottle sterilizing apparatus 30 that sterilizes any bottle 2 that has been blow-molded in the mold unit 20 that is at a temperature falling within the predetermined temperature range and has not been removed, an air-rinsing apparatus 34 that air-rinses the sterilized bottle 2, a filling apparatus 39 that fills the air-rinsed bottle 2 with a sterilized content, a lid member sterilizing apparatus 52 that sterilizes a lid member 3, which is a sealing member, a sealing apparatus 44 that seals the bottle 2 filled with the content with the sterilized lid member 3, a discharging apparatus 47 that discharges the sealed bottle 2 to the outside of the aseptic filling machine, and a conveying apparatus that conveys the supplied preform 1 and the molded bottle 2. The aseptic filling machine according to this embodiment of the present invention can achieve aseptic filling by filling a sterilized bottle 2 with a content sterilized in an aseptic atmosphere.

The heating apparatus 6, the blow-molding apparatus 16 and the bottle inspecting apparatus 24 are shielded by a molding portion chamber 12, the bottle sterilizing apparatus 30 is shielded by a sterilizing portion chamber 33, the air-rinsing apparatus 34 is shielded by an air-rinsing portion chamber 36, the filling apparatus 39 is shielded by a filling portion chamber 41, the sealing apparatus 44 is shielded by a sealing portion chamber 46, and the discharging apparatus 47 and a discharging conveyor 50 are shielded by a discharging portion chamber 49. An atmosphere separation chamber 27 is provided between the blow-molding apparatus 16 and the bottle sterilizing apparatus 30 to prevent a gas or mist of a sterilizer or a mixture thereof that occurs in the bottle sterilizing apparatus 30 from flowing into the blow-molding apparatus 16. By venting the atmosphere separation chamber 27, the gas or mist of a sterilizer or a mixture thereof that occurs in the bottle sterilizing apparatus 30 is prevented from flowing into the blow-molding apparatus 16. The filling apparatus 39 and the sealing apparatus 44 may be shielded by a single chamber. Further, the lid member sterilizing apparatus 52 and the sealing apparatus 44 may be shielded by the single chamber. Further, the sealing apparatus 44 and the discharging apparatus 47 may also be shielded by the single chamber.

During producing of products by the aseptic filling machine, aseptic air, which is made aseptic by a sterilizing filter, is supplied into the sterilizing portion chamber 33, the air-rinsing portion chamber 36, the filling portion chamber 41, the sealing portion chamber 46 and the discharging portion chamber 49. By supplying the aseptic air, the interior of the chambers is kept at a positive pressure, and the aseptic condition of the aseptic filling machine is maintained. The positive pressure is the highest in the filling portion chamber 41. The more upstream the chamber is located, such as the air-rinsing portion chamber 36 and the sterilizing portion chamber 33, the lower the positive pressure is set, and the more downstream the chamber is located, such as the sealing portion chamber 46 and the discharging portion chamber 49, the lower the positive pressure is set. The pressure in the atmosphere separation chamber 27 is substantially kept at the atmospheric pressure by venting the atmosphere separation chamber 27. For example, provided that the pressure in the filling portion chamber 41 is 20 Pa to 40 Pa, the pressures in the other chambers are lower than the pressure in the filling portion chamber 41.

In the aseptic filling machine, the preform 1 is heated, the heated preform 1 is sealed in the mold unit 20, which has a neck portion mold 20a, a trunk portion mold 20b and a bottom portion mold 20c, that is at a temperature falling within a predetermined temperature range, the preform 1 sealed in the mold unit 20 is blow-molded into a bottle, and any bottle 2 is removed which has been molded with the neck portion mold 20a, the trunk portion mold 20b and the bottom portion mold 20c the temperature of any of which is outside the predetermined temperature range. The aseptic filling machine includes the bottle removing apparatus 17 that removes a bottle 2. Although the bottle removing apparatus 17 is provided in the atmosphere separation chamber 27 in FIG. 1, the bottle removing apparatus 17 can be provided at any location where the bottle is not sterilized yet. Any bottle 2 that has been molded with the neck portion mold 20a, the trunk portion mold 20b and the bottom portion mold 20c all of which is at a temperature within the predetermined temperature range and has not been removed is sterilized by being brought into contact with a sterilizer. The contact of the bottle 2 with a sterilizer is achieved by blasting the sterilizer to inner and outer surfaces of the bottle 2. The blasted sterilizer is a gas or mist of a sterilizer, a mixture thereof, or a sterilizer in liquid form.

Preforms such as the preform 1 shown in FIG. 2(A) are successively conveyed from the preform supplying apparatus 4 shown in FIG. 1 to the heating apparatus 6 at a desired speed by a preform supply conveyor 5.

The preform 1 according to this embodiment is a bottomed cylindrical body having a test tube shape, and is formed with a mouth portion 1a like that of the bottle 2 shown in FIG. 2(D) in an early stage of the molding of the preform 1. A male thread is formed on the mouth portion 1a at the same time as the molding of the preform 1. Further, a support ring 1b used for conveyance is formed on the preform 1 below the mouth portion 1a. The preform 1 or the bottle 2 travels in the aseptic filling machine with the support ring 1b gripped by a gripper 22. The preform 1 is molded by injection molding, compression molding or the like. The preform 1 is made of a thermoplastic resin, such as polyethylene terephthalate, polyethylene naphthalate, polypropylene or polyethylene, and may contain a recycled thermoplastic resin. Further, to provide a barrier property, the preform 1 may include a layer of a thermoplastic resin, such as ethylene-vinyl alcohol copolymer or polyamide having metaxylylene diamine or other aromatic amine as a monomer, or may contain a mixture of the above-described materials.

The preform 1 supplied to the heating apparatus 6 is conveyed by wheels 7 and 8 on which a large number of grippers 22 are provided at a regular pitch and reaches a heating apparatus conveying wheel 9. At the heating apparatus conveying wheel 9, the preform 1 is released from the gripper 22 as shown in FIG. 2(B) and conveyed with a spindle 19 inserted into the mouth portion 1a of the preform 1.

As shown in FIG. 2(B), the preform 1 is heated to a temperature suitable for the subsequent blow molding by an infrared heater 14 or other heating device. The temperature is preferably 90° C. to 130° C.

The temperature of the mouth portion 1a of the preform 1 is kept to be equal to or lower than 70° C., in order to prevent deformation or the like of the mouth portion 1a.

As shown in FIG. 2(B), the preform 1 is conveyed by an endless chain 13 while being heated by the infrared heater 14 and rotated with the spindle 19 inserted into the mouth portion 1a. The spindles 19 are provided at regular intervals on the endless chain 13. The endless chain 13 rotates on pulleys 10 and 11. Instead of the spindle 19, a mandrel may be inserted into the preform 1 to rotate and convey the preform 1 in the inverted position.

The heated preform 1 is released from the spindle 19, gripped by the gripper 22, and conveyed to a molding wheel 18 in the blow-molding apparatus 16 via a wheel 15. As shown in FIG. 2(C), in the mold unit 20 on the molding wheel 18, the preform 1 is blow-molded into the bottle 2. The mold unit 20 has the neck portion mold 20a, the trunk portion mold 20b and the bottom portion mold 20c. The neck portion mold 20a and the trunk portion mold 20b are split molds and typically formed by a pair of two parts. The bottom portion mold 20c is typically formed by one piece. A plurality of mold units 20 and a plurality of blow nozzles 21 are arranged around the molding wheel 18, and rotate around the molding wheel 18 at a certain speed as the molding wheel 18 rotates.

When the heated preform 1 arrives, the mold unit 20 holds and seals the preform 1. After that, the blow nozzle 21 is connected to the preform 1, and an extension rod (not shown) is introduced into a hole formed in the blow nozzle 21 and inserted into the preform 1. The preform 1 is stretched lengthwise by the inserted extension rod, and at the same time is stretched crosswise by a gas, such as high-pressure air, blasted to the preform 1 from the blow nozzle 21. In this way, the preform 1 is molded into the bottle 2 in the mold unit 20. As shown in FIG. 2(D), the mold unit 20 is then opened, and the molded bottle 2 is removed from the mold unit 20, gripped at the support ring 1b by the gripper 22 provided on an inspection wheel 23 and passed to the inspection wheel 23.

The temperature of the neck portion mold 20a, the trunk portion mold 20b and the bottom portion mold 20c must be controlled to fall within the predetermined temperature range. When the heated preform 1 is blow-molded into the bottle 2, the surface temperature of the molded bottle 2 must be equal to or higher than a predetermined temperature. This is because if the surface temperature is lower than the predetermined temperature, the sterilization effect of the sterilizer that is blasted to and comes into contact with the surface of the bottle 2 can be inadequate. By controlling the temperature of a mold temperature adjusting medium that is circulated through the neck portion mold 20a, the trunk portion mold 20b and the bottom portion mold 20c to fall within the predetermined temperature range, the surface temperature of the bottle 2 can be controlled to be an appropriate temperature.

In order that the sterilizer blasted to the surface of the bottle 2 has an adequate sterilization effect, the surface temperature of the bottle 2 is equal to or higher than 40° C. or preferably equal to or higher than 50° C. when the sterilizer is blasted. More specifically, the surface temperature of the bottle 2 is equal to or higher than 40° C. or preferably equal to or higher than 50° C. immediately before the sterilizer is blasted to the bottle 2 that has been blow-molded, removed from the mold unit 20 and subjected to appearance inspection. In order that the surface temperature of the bottle 2 is equal to or higher than 40° C. immediately before the sterilizer is blasted, the surface temperature of the mold unit 20 is controlled to fall within the predetermined temperature range by a mold temperature adjusting apparatus 54.

Figure 5:
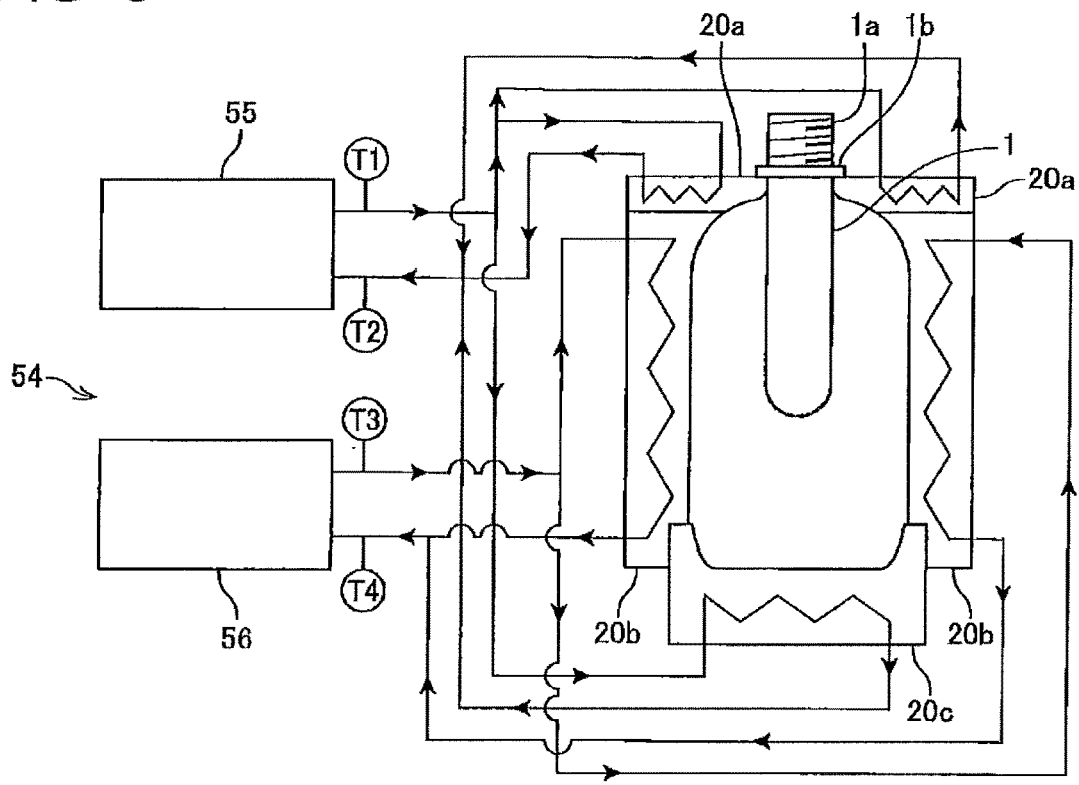
FIG. 5 shows a mold temperature adjusting apparatus provided in the aseptic filling machine according to the embodiment of the present invention.

As shown in FIG. 5, the mold temperature adjusting apparatus 54 is provided to adjust the temperature of the mold unit 20. The mold temperature adjusting apparatus 54 has a mold temperature adjusting medium cooling tank 55, a mold temperature adjusting medium heating tank 56, a conduit for introducing the mold temperature adjusting medium from the mold temperature adjusting medium cooling tank 55 to the neck portion mold 20a and the bottom portion mold 20c, a conduit for flowing the mold temperature adjusting medium from the mold temperature adjusting medium heating tank 56 to the trunk portion mold 20b, a pump for flowing the mold temperature adjusting medium to the conduits, a valve and a temperature sensor. By circulating the mold temperature adjusting medium through the mold unit 20, the mold temperature adjusting apparatus 54 controls the temperature of the neck portion mold 20a, the trunk portion mold 20b and the bottom portion mold 20c. The mold temperature adjusting apparatus 54 is provided with a circulation apparatus that circulates the mold temperature adjusting medium through the mold unit 20. The mold temperature adjusting medium is a liquid, such as water or oil. The mold temperature adjusting medium does not become 0° C. or lower or is not heated to high temperature, so that the mold temperature adjusting medium is preferably water.

By the mold temperature adjusting apparatus 54 controlling the temperature of the mold temperature adjusting medium to fall within the predetermined temperature range, the temperature of the mold unit 20 can be kept in the predetermined temperature range.

The mold temperature adjusting medium is cooled in the mold temperature adjusting medium cooling tank 55. An appropriate temperature range of the mold temperature adjusting medium is from 5° C. to 20° C. A cooling apparatus for cooling the mold temperature adjusting medium is provided in the mold temperature adjusting medium cooling tank 55. The mold temperature adjusting medium in the mold temperature adjusting medium heating tank 56 is kept in a temperature range from 40° C. to 70° C. A heating apparatus, such as a heater, for heating the mold temperature adjusting medium and a cooling apparatus for cooling the mold temperature adjusting medium having been heated are provided in the mold temperature adjusting medium heating tank 56.

As shown in FIG. 5, the mold temperature adjusting medium cooled in the mold temperature adjusting medium cooling tank 55 flows out of the mold temperature adjusting medium cooling tank 55 and is branched. One branch flow flows into two neck portion molds 20a, flows through a flow path in the neck portion molds 20a, flows out of the neck portion molds 20a and returns to the mold temperature adjusting medium cooling tank 55. Another branch flow flows into the bottom portion mold 20c, flows through a flow path in the bottom portion mold 20c, flows out of the bottom portion mold 20c and returns to the mold temperature adjusting medium cooling tank 55. The mold temperature adjusting medium need not be branched, and may flow from the mold temperature adjusting medium cooling tank 55 into the bottom portion mold 20c and then into the neck portion mold 20a.

The mouth portion 1a of the preform is not heated to a temperature equal to or higher than 70° C. in the heating apparatus 6. The neck portion mold 20a is a mold for molding a part of the preform 1 from below the support ring 1b to a shoulder portion of the bottle 2. The part of the preform 1 from below the support ring 1b to the shoulder portion of the bottle 2 that is to be molded is formed of a relatively large amount of resin and has a relatively high heat capacity for the area of the part after molding, so that the temperature of the part of the bottle 2 in contact with the neck portion mold 20a is less likely to decrease while the bottle 2 travels until the sterilizer is blasted thereto. The part of the preform 1 below the support ring 1b is heated to 90° C. to 130° C. by the heating apparatus 6. The temperature of the shoulder portion of the bottle 2 formed from the part of the preform 1 below the support ring 1b heated to 90° C. to 130° C. is around 70° C. or can be higher than 70° C., and the neck portion mold 20a needs to be cooled. To this end, in the mold temperature adjusting medium cooling tank 55, the mold temperature adjusting medium is kept in a temperature range from 5° C. to 20° C.

Since the temperature of the mold temperature adjusting medium circulated through the neck portion mold 20a is kept in the temperature range from 5° C. to 20° C., the surface temperature of the part of the bottle 2 from the part below the support ring 1b to the shoulder portion thereof is equal to or higher than 40° C. when the sterilizer is blasted to the bottle 2. If the temperature of the mold temperature adjusting medium in the mold temperature adjusting medium cooling tank 55 is lower than 5° C., the surface temperature of the part of the bottle 2 from the part below the support ring 1b to the shoulder portion may be lower than 40° C. when the sterilizer is blasted to the bottle 2. If the temperature of the mold temperature adjusting medium is higher than 20° C., the surface temperature of the part of the bottle 2 from the part below the support ring 1b to the shoulder portion may be higher than 70° C. when the sterilizer is blasted. If the bottle 2 is slowly cooled from a temperature higher than 70° C., the molded bottle 2 may be deformed.

A part of the preform 1 that is molded to form the bottom portion of the bottle 2 is heated to 90° C. to 130° C. by the heating apparatus 6. The bottom portion of the bottle 2 is formed by pressing and stretching the bottom portion of the preform 1 with an extension rod. Therefore, the bottom portion of the bottle 2 is thinner than the bottom portion of the preform 1. However, the bottom portion of the bottle 2 is thicker and has a higher heat capacity than the trunk portion of the bottle 2, and is not rapidly cooled by blow molding. When the bottom portion is slowly cooled, the resin forming the bottle 2 may crystalize, and the bottom portion may become brittle, so that the bottom portion mold 20c for molding the bottom portion of the bottle 2 is cooled in the blow molding. To this end, the mold temperature adjusting medium in the mold temperature adjusting medium cooling tank 55 is kept at a temperature of 5° C. to 20° C.

Since the mold temperature adjusting medium circulated through the bottom portion mold 20c is kept at a temperature of 5° C. to 20° C., the surface temperature of the bottom portion of the bottle 2 is equal to or higher than 40° C. when the sterilizer is blasted to the bottle 2. If the temperature of the mold temperature adjusting medium in the mold temperature adjusting medium cooling tank 55 is lower than 5° C., the surface temperature of the bottom portion of the bottle 2 may be lower than 40° C. when the sterilizer is blasted to the bottle 2. If the temperature of the mold temperature adjusting medium is higher than 20° C., crystallization may occur in the bottom part of the bottle 2, the bottom portion of the bottle 2 may become brittle, and the bottle 2 may be damaged due to drop impact. In addition, the bottom portion of the bottle 2 may also be deformed.

As shown in FIG. 5, the mold temperature adjusting medium heated in the mold temperature adjusting medium heating tank 56 flows into the upper portions of the two split parts of the trunk portion mold 20b, flows out of lower portions of the two parts of the trunk portion mold 20b, and then returns to the mold temperature adjusting medium heating tank 56. In the aseptic filling machine, immediately after the molding of the preform 1 into the bottle 2 is started, the mold temperature adjusting medium is heated in the mold temperature adjusting medium heating tank 56 and kept at a temperature of 40° C. to 70° C. However, as the number of times of the blow molding increases, the temperature of the mold temperature adjusting medium flowing out of the trunk portion mold 20b increases. The preform 1 heated to a temperature of 90° C. to 130° C. is stretched by high-pressure air, and the stretched resin at a temperature of 70° C. or higher is pressed against the trunk portion mold 20b. As a result, the temperature of the mold temperature adjusting medium tends to be higher than 70° C. To avoid this, the mold temperature adjusting medium heated in the mold temperature adjusting medium heating tank 56 is cooled and kept at a temperature of 40° C. to 70° C.

Since the mold temperature adjusting medium heated in the mold temperature adjusting medium heating tank 56 is kept at a temperature of 40° C. to 70° C., the surface temperature of the trunk portion of the bottle 2 is equal to or higher than 40° C. when the sterilizer is blasted to the bottle 2. If the temperature of the mold temperature adjusting medium in the mold temperature adjusting medium heating tank 56 is lower than 40° C., the surface temperature of the trunk portion of the bottle 2 may be lower than 40° C. when the sterilizer is blasted to the bottle 2. If the temperature of the mold temperature adjusting medium is higher than 70° C., the glass transition point of the resin forming the bottle 2 may be exceeded before the bottle is removed from the mold unit 20, and bleaching may occur in the trunk portion of the bottle 2 when the bottle 2 removed from the mold unit 20 is slowly cooled.

The neck portion mold 20a and the bottom portion mold 20c have an inlet and an outlet for the mold temperature adjusting medium at substantially the same level, so that the mold temperature adjusting medium can flow into the neck portion mold 20a and the bottom portion mold 20c at any part thereof. As for the trunk portion mold 20b, although the mold temperature adjusting medium flows into the trunk portion mold 20b at an upper part thereof and flows out of the trunk portion mold 20b at a lower part thereof in FIG. 5, the mold temperature adjusting medium may flows into the trunk portion mold 20b at a lower part thereof and flow out of the trunk portion mold 20b at an upper part thereof. The aseptic filling machine is provided with a plurality of the mold units 20, and the mold temperature adjusting medium is flowed into all the mold units 20 to control the temperature of the mold units 20. Typically, the aseptic filling machine is provided with four to thirty-six mold units 20.

A temperature sensor is provided in the mold temperature adjusting medium cooling tank 55 and the mold temperature adjusting medium heating tank 56 as a mold temperature adjusting medium temperature measuring apparatus that measures the temperature of the mold temperature adjusting medium, and based on the temperature information from the temperature sensor, the temperature of the mold temperature adjusting medium in the mold temperature adjusting medium cooling tank 55 and the mold temperature adjusting medium heating tank 56 is adjusted and kept in the predetermined range. The mold temperature adjusting apparatus 54 is provided with another separate temperature sensor as a mold temperature adjusting medium temperature measuring apparatus in the flow path of the mold temperature adjusting medium. By providing the temperature sensor in the flow path of the mold temperature adjusting medium, the temperature of the mold temperature adjusting medium flowing into and flowing out of the mold unit 20 can be kept track of.

A temperature sensor T1 is provided at a location where the mold temperature adjusting medium flows out of the mold temperature adjusting medium cooling tank 55, and a temperature sensor T2 is provided at a location where the mold temperature adjusting medium flows into the mold temperature adjusting medium cooling tank 55. A temperature sensor T3 is provided at a location where the mold temperature adjusting medium flows out of the mold temperature adjusting medium heating tank 56, and a temperature sensor T4 is provided at a location where the mold temperature adjusting medium flows into the mold temperature adjusting medium heating tank 56.

When the temperature indicated by the temperature sensor T1 or T2 is outside the range from 5° C. to 20° C., or when the temperature indicated by the temperature sensor T3 or T4 is outside the range from 40° C. to 70° C., or when both the temperature indicated by the temperature sensor T1 or T2 and the temperature indicated by the temperature sensor T3 or T4 are outside the respective ranges, there is a possibility that the surface temperature of the bottle 2 to which the sterilizer is blasted is not equal to or higher than 40° C. or a possibility that the bottle 2 is deformed, so that the blow-molded bottle 2 is removed to the outside of the aseptic filling machine by the bottle removing apparatus 17 and is not conveyed to the bottle sterilizing apparatus 30. When the measured temperature of the mold temperature adjusting medium is outside the predetermined temperature range, the circulation of the mold temperature adjusting medium through the mold unit 20 can be stopped.

Figure 6:
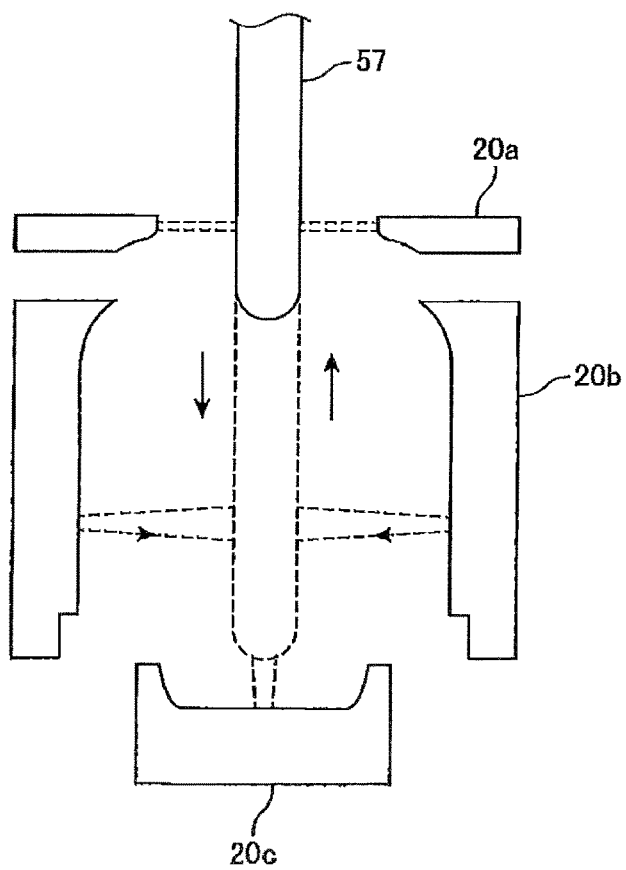
FIG. 6 shows a mold surface temperature measuring apparatus being inserted into a mold unit provided in the aseptic filling machine according to the embodiment of the present invention.

Although it has been described that the temperature of the mold unit 20 is controlled by regarding the temperature of the mold temperature adjusting medium circulating through the mold unit 20 as the temperature of the mold unit 20, the surface temperature of the mold unit 20 may be directly measured and regarded as a mold temperature. FIG. 6 shows a mold surface temperature measuring apparatus 57 that measures the surface temperature of the mold unit 20 with a non-contact thermometer. The mold surface temperature measuring apparatus 57 measures the surface temperature of the open mold unit 20 immediately after the blow-molded bottle 2 is removed. The surface temperature of the mold unit 20 is measured by inserting the mold surface temperature measuring apparatus 57 into the open mold unit 20 from above the mold unit 20.

The surface temperature of the neck portion mold 20a and the bottom portion mold 20c is preferably kept in the temperature range from 5° C. to 20° C. If the surface temperature of the neck portion mold 20a or the bottom portion mold 20c is lower than 5° C., the temperature of the mold temperature adjusting medium in the mold temperature adjusting medium cooling tank 55 is raised to increase the surface temperature of the neck portion mold 20a and the bottom portion mold 20c to 5° C. or higher. If the surface temperature of the neck portion mold 20a or the bottom portion mold 20c is higher than 20° C., the mold temperature adjusting medium in the mold temperature adjusting medium cooling tank 55 is cooled to decrease the surface temperature of the neck portion mold 20a and the bottom portion mold 20c to 20° C. or lower.

The surface temperature of the trunk portion mold 20b is preferably kept in the temperature range from 40° C. to 70° C. If the surface temperature of the trunk portion mold 20b is lower than 40° C., the temperature of the mold temperature adjusting medium in the mold temperature adjusting medium heating tank 56 is raised to increase the surface temperature of the trunk portion mold 20b to 40° C. or higher. If the surface temperature of the trunk portion mold 20b is higher than 70° C., the mold temperature adjusting medium in the mold temperature adjusting medium heating tank 56 is cooled to decrease the surface temperature of the trunk portion mold 20b to 70° C. or lower.

The mold surface temperature measuring apparatus 57 has at least three sensors including the sensor that measures the surface temperature of the bottom portion mold 20c and the two sensors that move vertically and measure the surface temperature of the neck portion mold 20a and the trunk portion mold 20b, which are split molds each formed by two parts. When separately measuring each part of the neck portion mold 20a and the trunk portion mold 20b, the mold surface temperature measuring apparatus 57 has five sensors.

The temperature sensor measures temperature by sensing the infrared radiation emitted from the mold unit 20. However, the present invention is not limited to this. Although it had been difficult to measure the temperature of a mirror-like metal surface, such as the surface of the mold unit 20, because of its low emissivity, sensors capable of measuring the temperature of such a surface have been recently developed.

The sensor can measure temperature with high precision when the tip end of the sensor is directed normal to the measured surface of the mold unit 20. The angle formed by a straight line extending from the tip end of the sensor and the normal to the measured surface is preferably 30 degrees or less, or 60 degrees or less at the maximum. If the angle is greater than 60 degrees, the area of the part of the mold unit 20 in which the surface temperature is to be measured is too large, and it is difficult to measure the temperature with high accuracy.

The surface temperature of the bottom portion mold 20c can be directly measured by the sensor provided at the tip end of the mold surface temperature measuring apparatus 57. When measuring the surface temperature of the neck portion mold 20a and the trunk portion mold 20b, the tip end of the sensor is not directed perpendicularly to the measured surface. However, a mirror that reflects the infrared radiation emitted from the measured surface at an angle of 90 degrees can be attached to the tip end of the sensor to enable measurement of the surface temperature of the neck portion mold 20a and the trunk portion mold 20b, which are located at the sides of the mold surface temperature measuring apparatus 57. Provided that the diameter of the sensor is 15 mmϕ, for example, the total width of two sensors incorporated in the mold surface temperature measuring apparatus 57 is about 30 mm, and the sensors can be inserted into the open mold unit 20. The sensor for the bottom portion mold 20c and the sensors for the neck portion mold 20a and the trunk portion mold 20b are incorporated in different parts of the mold surface temperature measuring apparatus 57, so that the mold surface temperature measuring apparatus 57 does not have to have a width greater than 30 mm.

As shown in FIG. 6, after the mold surface temperature measuring apparatus 57 is inserted into the mold unit 20, the surface temperature of the neck portion mold 20a, the trunk portion mold 20b and the bottom portion mold 20c while lowering the mold surface temperature measuring apparatus 57 incorporating at least three sensors. Alternatively, the mold surface temperature measuring apparatus 57 incorporating five temperature sensors may be inserted into the mold unit 20 to measure the surface temperature of five parts of the mold unit 20 at the same time. The mold surface temperature measuring apparatus 57 need not be provided for all of the molds.

Instead of inserting the mold surface temperature measuring apparatus 57 into the mold unit 20 from above the mold unit 20, the mold surface temperature measuring apparatus 57 may be inserted into the open mold unit 20 from a side of the open mold unit 20 to measure the surface temperature of the mold unit 20.

Figure 7:
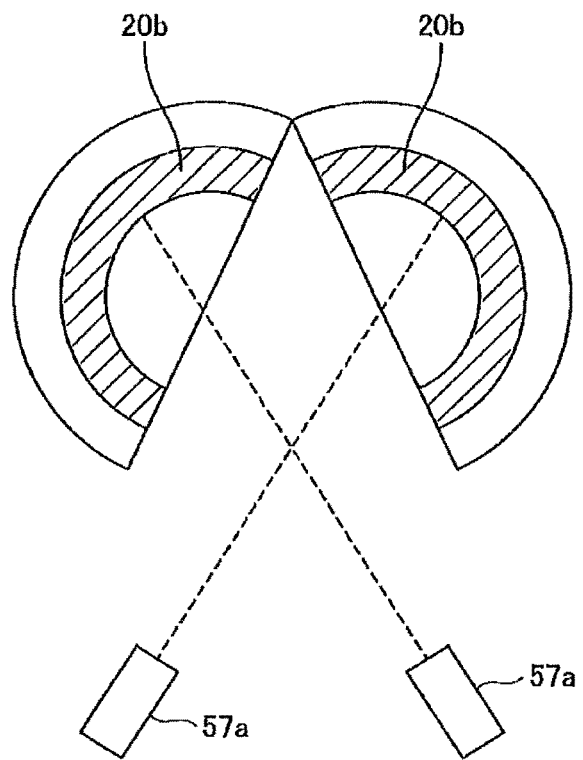
FIG. 7 shows a mold surface temperature measuring apparatus measuring, from outside, a trunk portion mold provided in the aseptic filling machine according to the embodiment of the present invention.

The mold surface temperature measuring apparatus 57 does not have to be inserted into the mold unit 20 to measure the surface temperature of the mold unit 20. As shown in FIG. 7, after the mold unit 20 is opened after blow molding and the bottle 2 is removed, the surface temperature of the mold unit 20 may be measured from outside the mold unit 20 with a mold surface temperature measuring apparatus 57a. As shown in FIG. 7, at least two mold surface temperature measuring apparatuses 57a are provided to measure the surface temperature of the trunk portion mold 20b. Although FIG. 7 shows a mold unit for forming a round-shape bottle 2, the mold unit can be any mold unit for forming a bottle having a rectangular or polygonal shape.

Figure 8:
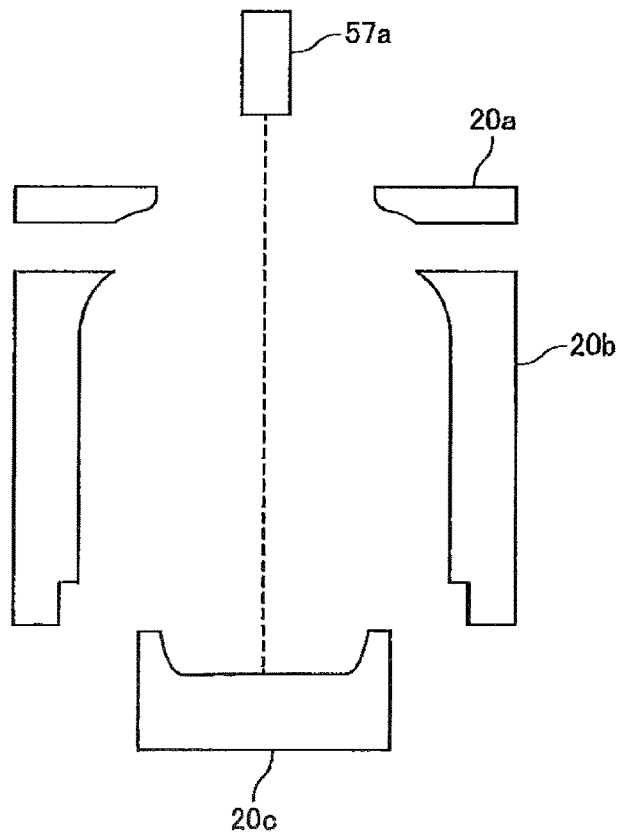
FIG. 8 shows the mold surface temperature measuring apparatus measuring, from outside, a bottom portion mold provided in the aseptic filling machine according to the embodiment of the present invention.

As shown in FIG. 8, if the mold surface temperature measuring apparatus 57a that receives the infrared radiation traveling perpendicularly from the surface of the bottom portion mold 20c is provided above the mold unit 20, the surface temperature of the bottom portion mold 20c can be measured without inserting the mold surface temperature measuring apparatus 57 into the mold unit 20.

All the measured temperatures of the mold unit 20 measured by the mold surface temperature measuring apparatus 57 or the mold surface temperature measuring apparatus 57a must be equal to or higher than 40° C. If all the temperatures of the five parts of the neck portion mold 20a, the trunk portion mold 20b and the bottom portion mold 20c are not equal to or higher than 40° C., there is a possibility that the surface temperature of the bottle 2 to which the sterilizer is blasted is not equal to or higher than 40° C., and the bottle 2 blow-molded at this timing is removed to the outside of the aseptic filling machine by the bottle removing apparatus 17 and is not conveyed to the bottle sterilizing apparatus 30. If all the temperatures are equal to or higher than 40° C., which is the predetermined temperature, the bottle 2 is conveyed to the bottle sterilizing apparatus 30.

The bottle 2 passed to the inspection wheel 23 is subjected to appearance inspection by the bottle inspecting apparatus 24. The bottle inspecting apparatus 24 is provided around the inspection wheel 23 and inspects the trunk portion, the support ring 1b, the top face of the mouth portion 1a, the bottom portion and the like of the molded bottle 2. If it is determined that the bottle 2 has an abnormality, the bottle removing apparatus 17 removes the bottle 2 to the outside of the aseptic filling machine.

The bottle trunk portion, the support ring 1b, the mouth portion 1a of the bottle 2, the top face of the bottle 2, and the bottom portion of the bottle 2 are imaged by a camera to inspect the condition of these portions. The taken image is processed by an image processing apparatus to determine whether there is any abnormality, such as a scratch, a foreign matter, deformation, or discoloration. Any bottle 2 for which any of these is outside the allowable range is determined to be abnormal.

Any bottle 2 inspected by the bottle inspecting apparatus 24 and not determined to be abnormal is conveyed to the bottle sterilizing apparatus 30 via wheels 25 and 26 in the atmosphere separation chamber 27 that is provided between the blow-molding apparatus 16 and the bottle sterilizing apparatus 30 to prevent the sterilizer used in the bottle sterilizing apparatus 30 from flowing into the blow-molding apparatus 16.

The wheel 25 is provided with the bottle removing apparatus 17, which removes any bottle 2 that has been molded with the neck portion mold 20a, the trunk portion mold 20b and the bottom portion mold 20c the temperature of any of which is outside the predetermined temperature range. That is, when the temperature of the mold temperature adjusting medium flowing into or flowing out of any of the neck portion mold 20a, the trunk portion mold 20b and the bottom portion mold 20c is outside the predetermined temperature range, the molded bottle 2 is removed to the outside of the aseptic filling machine by the bottle removing apparatus 17. Further, when the measured surface temperature of any of the neck portion mold 20a, the trunk portion mold 20b and the bottom portion mold 20c is outside the predetermined temperature range, the molded bottle 2 is removed. Further, any bottle 2 determined to be abnormal by the inspection apparatus is also removed.

The bottle 2 conveyed to the bottle sterilizing apparatus 30 is sterilized on the wheel 28. The sterilization is achieved by bringing the sterilizer into contact with the bottle 2, or specifically, by blasting the sterilizer to the bottle 2. A step of blasting the sterilizer to the bottle 2 to sterilize the bottle 2 is shown in FIG. 3(E-1). To blast the sterilizer to the bottle 2, a sterilizer blasting nozzle 31 is provided. The sterilizer blasting nozzle 31 is fixed in such a manner that a nozzle hole at the tip end thereof can be directly opposed to the opening of the mouth portion 1a of the bottle 2 traveling directly below the sterilizer blasting nozzle 31. As required, a sterilizer blasting tunnel 32 is provided below the sterilizer blasting nozzle 31 along the travel path of the bottle 2 as shown in FIG. 3(E-1). One or more sterilizer blasting nozzles 31 can be provided. The sterilizer blasted to the bottle 2 flows into the bottle 2 and sterilizes the inner surface of the bottle 2. At the same time, the bottle 2 travels in the sterilizer blasting tunnel 32, and the sterilizer also flows onto the outer surface of the bottle 2 and sterilizes the outer surface of the bottle 2.

When the sterilizer is a gas or mist of a sterilizer or a mixture thereof, as shown in FIG. 3(E-1), the bottle 2 can be in the upright position. However, the sterilizer in liquid form is blasted, the bottle 2 is inverted and gripped by the gripper 22 at the support ring 1b thereof, and the sterilizer is blasted to the inner surface of the bottle 2 through the mouth portion 1a from a nozzle facing upward, in order that the sterilizer comes into contact with entire inner surface of the bottle 2. In addition, the sterilizer is blasted to the outer surface of the bottle 2 from a nozzle facing downward, in order that the sterilizer comes into contact with the entire outer surface of the bottle 2. The nozzle facing upward may be arranged to be opposed to the mouth portion 1a of the bottle 2 or may be arranged to move at the same speed as the bottle 2 being conveyed and inserted into the bottle 2. A plurality of nozzles facing downward may be provided.

As shown in FIG. 3(E-2), the sterilizer blasting nozzle 31 may move along with the bottle 2 being conveyed and the sterilizer blasting nozzle 31 may be inserted into the bottle 2 to directly blast the sterilizer to the inner surface of the bottle 2. Any sterilizer overflowing from the bottle 2 collides against a guide member 31a provided to surround the sterilizer blasting nozzle 31, flows onto the outer surface of the bottle 2 and comes into contact with the outer surface of the bottle 2. The guide member 31a is provided with a flange portion that is coaxial with the nozzle 31 and an annular wall portion that protrudes from the flange portion along the circumference thereof.

Figure 4:
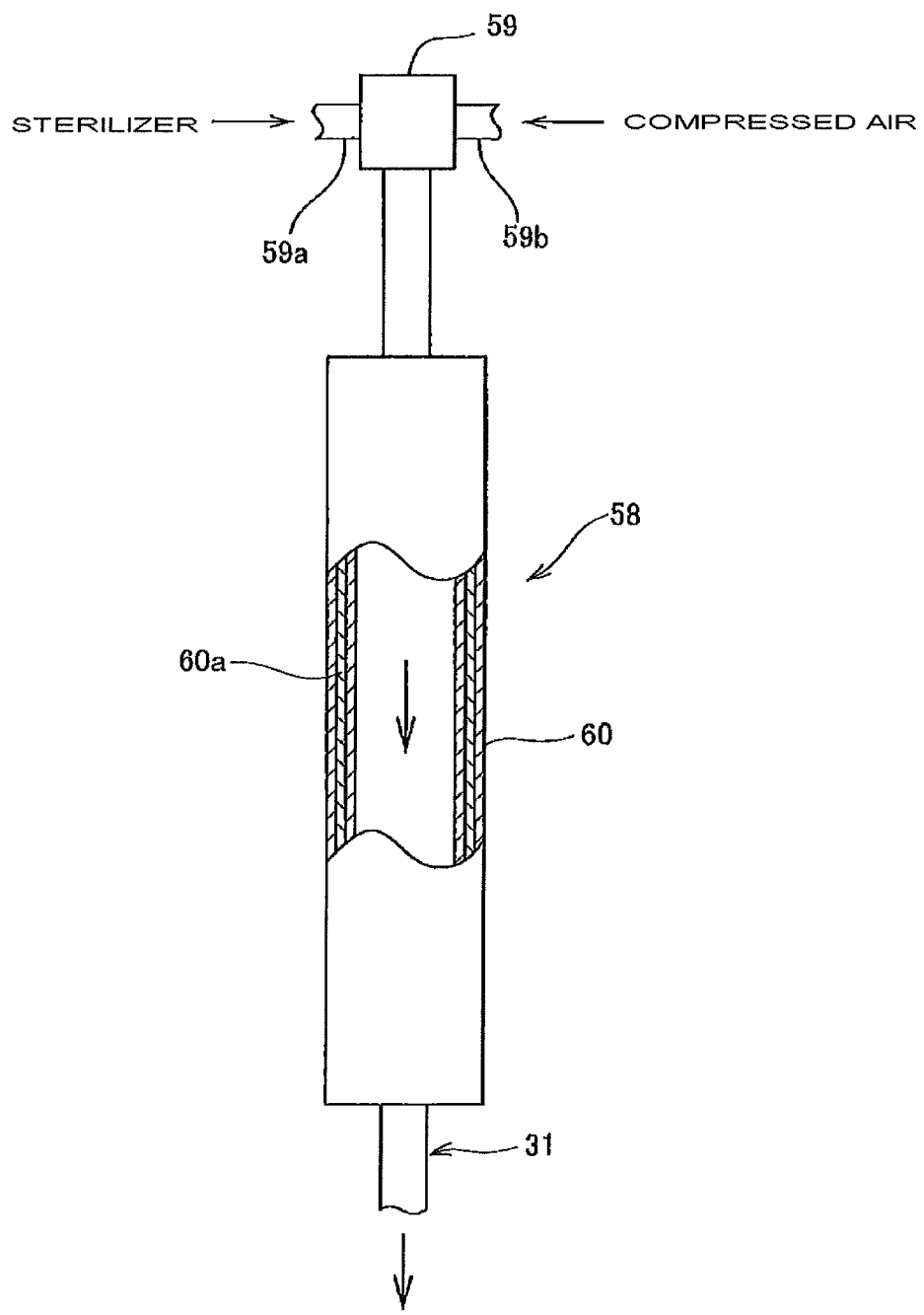
FIG. 4 shows a sterilizer gas generator incorporated in the aseptic filling machine according to the embodiment of the present invention.

The gas or mist of the sterilizer or a mixture thereof is the sterilizer gasified by a sterilizer gas generator 58 shown in FIG. 4, or a mist formed by condensation of the gasified sterilizer, or a mixture thereof. The sterilizer gas generator 58 includes a sterilizer supply portion 59 that is a twin-fluid spray nozzle that supplies a sterilizer in the form of drops, and a vaporizing portion 60 that vaporizes the sterilizer supplied from the sterilizer supply portion 59 by heating the sterilizer to a temperature equal to or lower than the decomposition temperature thereof. The sterilizer supply portion 59 is configured to guide the sterilizer and compressed air that are introduced from a sterilizer supply path 59a and a compressed air supply path 59b, respectively, and spray the sterilizer into the vaporizing portion 60. The vaporizing portion 60 is a pipe that incorporates a heater 60a disposed between inner and outer walls thereof, and heats and vaporizes the sterilizer blasted into the pipe. The gas of the vaporized sterilizer is ejected to the outside of the vaporizing portion 60 from the sterilizer gas blasting nozzle 31. The vaporizing portion 60 may be heated by induction heating instead of the heater 60a.

As the operating condition of the sterilizer supply portion 59, for example, the pressure of the compressed air is adjusted within the range of 0.05 MPa to 0.6 MPa. The sterilizer may be supplied by gravity or pressure, and the amount of the supplied sterilizer can be arbitrarily set. For example, the sterilizer is supplied to the sterilizer supply path 59a in an amount in a range of 1 g/min. to 100 g/min. Furthermore, the sprayed sterilizer is vaporized by heating the inner surface of the vaporizing portion 60 to a temperature from 140° C. to 450° C.

As shown in FIG. 3(E-1) and FIG. 3(E-2), the sterilizer gas is blasted from the sterilizer blasting nozzle 31 to the bottle 2. Although the blasting amount of the gas or mist of the sterilizer or a mixture thereof is arbitrarily set, the blasting amount is determined by the amount of the sterilizer supplied to the sterilizer gas generator 58 and the duration of blasting. A plurality of sterilizer gas generators 58 may be provided. The blasting amount also depends on the size of the bottle 2.

The sterilizer blasted to the bottle 2 in the form of gas or mist, or a mixture thereof preferably contains at least hydrogen peroxide. An appropriate range of the content of hydrogen peroxide is from 0.5% by mass to 65% by mass. If the content is lower than 0.5% by mass, the sterilization power may be insufficient in some cases, while if the content is higher than 65% by mass, the sterilizer will be difficult to handle from the viewpoint of safety. A further preferable range is from 0.5% by mass to 40% by mass. When the content is equal to or lower than 40% by mass, it is easier to handle the sterilizer, and the residual amount of the sterilizer in the bottle 2 after sterilization can be reduced since the concentration of hydrogen peroxide is low.

When a hydrogen peroxide solution is used as the sterilizer, the blasting amount of the gas of the hydrogen peroxide solution is as follows. The amount of the hydrogen peroxide adhering to the inner surface of the bottle 2 that derives from the gas of the hydrogen peroxide solution blasted to the inner surface of the bottle 2 from the sterilizer blasting nozzle 31 is preferably within a range of 30 μL/bottle to 150 μL/bottle, and more preferably within a range of 50 μL/bottle to 100 μL/bottle, when the hydrogen peroxide solution contains 35% by mass of hydrogen peroxide. The hydrogen peroxide concentration of the gas of the hydrogen peroxide solution blasted to the bottle 2 is preferably within a range of 2 mg/L to 20 mg/L, and more preferably within a range of 5 mg/L to 10 mg/L.

When the liquid sterilizer is blasted to the bottle 2, the sterilizer preferably contains peracetic acid. Further, the liquid sterilizer is preferably a balanced peroxide composition composed of peracetic acid, hydrogen peroxide, acetic acid and water. The concentration of peracetic acid is preferably from 500 mg/L to 4000 mg/L. If the concentration thereof is lower than 500 mg/L, the sterilization power is insufficient, while if the concentration thereof is higher than 4000 mg/L, the excessively high concentration of peracetic acid can cause deterioration of members such as packings in the aseptic filling machine.

The liquid sterilizer is heated to 50° C. to 80° C., and is preferably heated to 60° C. to 70° C. The heated sterilizer has an improved sterilization effect. The appropriate flowrate of each sterilizer blasting nozzle 31 is from 1 L/min. to 15 L/min., and is preferably from 3 L/min. to 10 L/min. The duration of blasting is appropriately from 0.2 seconds to 5 seconds. The amount of the liquid sterilizer blasted to the bottle 2 is determined by the flowrate to the sterilizer blasting nozzle 31 and the duration of blasting, and is preferably from 0.05 ml/cm$^2$ to 20 ml/cm$^2$ with respect to the surface area of the bottle 2. If the amount is lower than 0.05 ml/cm$^2$, the sterilization power is insufficient, while if the amount is higher than 20 ml/cm$^2$, the amount is excessive, leading to waste of energy and sterilizer.

The sterilizer contains water. However, the sterilizer may contain one or more of alcohols such as methyl alcohol, ethyl alcohol, isopropyl alcohol, n-propyl alcohol and butyl alcohol, ketones such as acetone, methyl ethyl ketone and acetylacetone, and glycol ethers and the like.

The sterilizer may further contain an additive agent such as a compound having a sterilizing effect such as an organic acid, a chlorine compound including sodium hypochlorite or ozone, a cationic surface active agent, a non-ionic surface active agent, or a phosphate compound.

The bottle 2 sterilized in the bottle sterilizing apparatus 30 is conveyed to the air-rinsing apparatus 34 via a wheel 29, as shown in FIG. 1. On an air-rinsing wheel 35 shown in FIG. 1, the bottle 2 is in the upright position, and aseptic air is blasted to the bottle 2 from an air-rinsing nozzle 38 as shown in FIG. 3(F-1). Although the aseptic air can be at room temperature, the aseptic air is preferably heated. The aseptic air has effects of discharging any sterilizer remaining in the bottle 2, decomposing the remaining sterilizer to increase the sterilization effect, and discharging any foreign matter in the bottle 2. Alternatively, the aseptic air may be blasted to the bottle 2 in the inverted position as shown in FIG. 3(F-2). In the inverted position, foreign matters can be more effectively discharged than in the upright position. Further, if a guide member that surrounds the air-rinsing nozzle 38 is provided as with the sterilizer blasting nozzle 31 in FIG. 3(E-2), the aseptic air introduced into the bottle 2 and then overflowing from the mouth portion 1a collides against the guide member and also rinses the outer periphery of the mouth portion 1a, so that the temperature of the outer periphery of the mouth portion 1a rises, and the outer periphery of the mouth portion 1a is more effectively sterilized.

The air-rinsing nozzle 38 may be capable of vertical movement and may blast aseptic air into the bottle 2 while moving vertically. Instead of the aseptic air, aseptic water may be introduced into the bottle 2 to rinse the inside of the bottle 2. Further, both the aseptic air and the aseptic water may be used in combination to rinse the bottle 2.

The bottle 2 having come into contact with the sterilizer is rinsed with aseptic water to remove the adhering sterilizer. The aseptic water is produced by heating water to a temperature equal to or higher than 121° C. for four or more minutes, or passing water through a sterilizing filter. The rinsing of the bottle 2 with aseptic water is performed in a manner similar to the manner of blasting the sterilizer by an apparatus similar to that used for the blasting of the sterilizer. In order that the entire inner surface of the bottle 2 is rinsed with the aseptic water, the support ring 1b of the inverted bottle 2 is gripped by a gripper 22, and the aseptic water is blasted from a nozzle facing upward to the inner surface of the bottle 2 through the mouth portion 1a. In order that the entire outer surface of the bottle 2 is rinsed with the aseptic water, the aseptic water is blasted from a nozzle facing downward to the outer surface of the bottle 2. The nozzle facing upward may be arranged to be opposed to the mouth portion 1a of the bottle 2 or may be arranged to move at the same speed as the bottle 2 being conveyed and inserted into the bottle 2. A plurality of nozzles facing downward may be provided.

The temperature of the aseptic water is adjusted to fall within a range of 10° C. to 80° C. or preferably a range of 30° C. to 70° C. The flowrate of the aseptic water blasted from each nozzle is from 1 L/min. to 15 L/min., or preferably from 3 L/min. to 10 L/min. The duration of blasting is appropriately from 0.1 seconds to 15 seconds. The amount of the aseptic water blasted to the bottle 2 is determined by the flowrate of the nozzles and the duration of blasting, and is preferably from 0.05 ml/cm$^2$ to 20 ml/cm$^2$ with respect to the surface area of the bottle 2. If the amount is lower than 0.05 ml/cm$^2$, the rinsing is inadequate, while if the amount is higher than 20 ml/cm$^2$, energy is wasted.

The bottle 2 having been air-rinsed by the air-rinsing apparatus 34 is conveyed to the filling apparatus 39 via a wheel 37, as shown in FIG. 1. In the filling apparatus 39, on a filling wheel 40 shown in FIG. 1, the bottle 2 is filled with a content by a filling nozzle 42 in a filling step shown in FIG. 3(G). The content is sterilized in advance, and the bottle 2 is filled with a certain amount of content, such as a drink, by the filling nozzle 42 traveling in synchronization with the bottle 2.

The bottle 2 filled with the content is conveyed to the sealing apparatus 44 via a wheel 43 shown in FIG. 1. In the sealing apparatus 44, in a sealing step shown in FIG. 3(H), the lid member 3, which is a sealing member sterilized by the lid member sterilizing apparatus 52, is supplied to a sealing wheel 45 through a sterilized lid member conveyance path 51 and via a lid supplying wheel 53a and a lid receiving wheel 53b, and is wrapped around and fastened to the mouth portion 1a of the bottle 2 by a capper (not shown) to seal the bottle 2.

The sealed bottle 2 is passed from the gripper 22 on the sealing wheel 45 to the gripper 22 on a discharging wheel 48 of the discharging apparatus 47. The bottle 2 having passed to the discharging wheel 48 is placed on the discharging conveyor 50. The bottle 2 placed on the discharging conveyor 50 is discharged to the outside of the aseptic filling machine.

The interior of the sterilizing portion chamber 33, the air-rinsing portion chamber 36, the filling portion chamber 41, the sealing portion chamber 46 and the discharging portion chamber 49 is sterilized before operation of the aseptic filling machine.

The sterilizer is blasted into each chamber that needs to be sterilized in such a manner that the sterilizer adheres to the entire interior of the chamber. The blasted sterilizer sterilizes the interior of each chamber. The same sterilizer as that used for sterilizing the bottle 2 can be used, and a sterilizer containing peracetic acid or hydrogen peroxide is preferably used. A plurality of times of blasting sterilizers may be performed to separately blast different sterilizers.

Although the present invention is configured as described above, the present invention is not limited to the embodiment described above, and various modifications can be made without departing from the spirit of the present invention.

REFERENCE SIGNS LIST 1 preform
2 bottle
6 heating apparatus
16 blow-molding apparatus
17 bottle removing apparatus
20 mold unit
20a neck portion mold
20b trunk portion mold
20c bottom portion mold
30 bottle sterilizing apparatus
39 filling apparatus
44 sealing apparatus
49 discharging portion chamber
54 mold temperature adjusting apparatus
55 mold temperature adjusting medium cooling tank
56 mold temperature adjusting medium heating tank
57 mold surface temperature measuring apparatus

The invention claimed is:

1. An aseptic filling method, comprising:
heating a preform;
sealing the heated preform in a sealing apparatus including a neck portion mold, a trunk portion mold and a bottom portion mold at a temperature in a predetermined temperature range;
blow molding the preform sealed in the molds into a bottle;
measuring a mold surface temperature of the neck portion mold, the trunk portion mold, and the bottom mold portion with a mold surface temperature measuring apparatus;
removing, by a bottle removing apparatus, any bottle molded in the neck portion mold, the trunk portion mold and the bottom portion mold when the mold surface temperature of any of the neck portion mold, the trunk portion mold and the bottom portion mold is outside of the predetermined temperature range as measured by the mold surface temperature measuring apparatus;

contacting any bottle that has not been removed with a sterilizer to sterilize a surface of the bottle;

filling the sterilized bottle with a sterilized content; and sealing the sterilized bottle filled with the sterilized content with a sterilized lid member.

2. The aseptic filling method according to claim 1, wherein said mold surface temperature measuring apparatus comprises a sensor having a tip end configured for sensing an infrared radiation emitted from a surface of the mold portions, and wherein an angle formed by a straight line extending from the tip end of the sensor and normal to a measured surface of the mold portions is equal to or less than 60 degrees.

3. The aseptic filling method according to claim 2, wherein the mold surface temperature of the molds is a temperature of the molds opened immediately after the preform is blow-molded into the bottle.

4. The aseptic filling method according to claim 3, wherein the sterilizer is a gas or mist of a sterilizer or a mixture thereof.

5. The aseptic filling method according to claim 2, wherein the sterilizer is a gas or mist of a sterilizer or a mixture thereof.

6. The aseptic filling method according to claim 1, wherein the mold surface temperature of the neck portion mold, the trunk portion mold and the bottom portion mold in the predetermined temperature range is a temperature of a mold temperature adjusting medium circulated through the molds.

7. The aseptic filling method according to claim 6, wherein the sterilizer is a gas or mist of a sterilizer or a mixture thereof.

8. The aseptic filling method according to claim 1, wherein the sterilizer is a gas or mist of a sterilizer or a mixture thereof.

9. An aseptic filling machine, comprising:

a heating apparatus that heats a preform;

a sealing apparatus having a neck portion mold, a trunk portion mold and a bottom portion mold in which the heated preform is sealed;

a mold temperature adjusting apparatus that adjusts a mold surface temperature of the neck portion mold, the trunk portion mold and the bottom portion mold to be within a predetermined temperature range;

a blow-molding apparatus that blow-molds the heated preform sealed in the molds into a bottle;

a mold surface temperature measuring apparatus for measuring a mold surface temperature of the neck portion mold, the trunk portion mold, and the bottom mold portion;

a bottle removing apparatus that removes any bottle that has been molded in the neck portion mold, the trunk portion mold and the bottom portion mold when the mold surface temperature of any of the neck portion mold, the trunk portion mold and the bottom portion mold is outside of the predetermined temperature range as measured by the mold surface temperature measuring apparatus;

a bottle sterilizing apparatus that sterilizes any bottle that has not been removed by blasting a sterilizer to the bottle;

a filling apparatus that fills the sterilized bottle with a sterilized content;

a sealing apparatus that seals the sterilized bottle filled with the sterilized content with a sterilized lid member; and a conveying apparatus that conveys the preform or the bottle from the heating apparatus to the sealing apparatus.

10. The aseptic filling machine according to claim 9, wherein the mold temperature adjusting apparatus comprises the mold surface temperature measuring apparatus that measures the mold surface temperature of the neck portion mold, the trunk portion mold and the bottom portion mold, wherein the mold surface temperature measuring apparatus comprises a sensor having a tip end configured for sensing an infrared radiation emitted from a surface of the mold portions, and wherein an angle formed by a straight line extending from the tip end of the sensor and normal to a measured surface of the mold portions is equal to or less than 60 degrees.

11. The aseptic filling machine according to claim 10, wherein the mold surface temperature measuring apparatus measures a surface temperature of an inner surface of the neck portion mold, the trunk portion mold and the bottom portion mold opened immediately after the preform is blow-molded into the bottle.

12. The aseptic filling machine according to claim 9, wherein the mold temperature adjusting apparatus comprises a circulating apparatus that circulates a mold temperature adjusting medium through the neck portion mold, the trunk portion mold and the bottom portion mold, and a mold temperature adjusting medium temperature measuring apparatus that measures a temperature of the mold temperature adjusting medium for all of the molds when the mold temperature adjusting medium flows into and flows out of each of the neck portion mold, the trunk portion mold and the bottom portion mold.

13. The aseptic filling machine according to claim 12, wherein the mold temperature adjusting apparatus stops circulating the mold temperature adjusting medium through the molds when the temperature of the mold temperature adjusting medium flowing into and flowing out of the molds is outside the predetermined temperature range.

* * * * *